(12) United States Patent
Sohngen

(10) Patent No.: US 8,092,454 B2
(45) Date of Patent: Jan. 10, 2012

(54) FIXATION INSTRUMENT FOR TREATING A BONE FRACTURE

(76) Inventor: Gary W. Sohngen, San Pedro, CA (US)

( * ) Notice: Subject to any disclaimer, the term of this patent is extended or adjusted under 35 U.S.C. 154(b) by 166 days.

(21) Appl. No.: 11/078,750

(22) Filed: Mar. 11, 2005

(65) Prior Publication Data

US 2005/0203510 A1 Sep. 15, 2005

Related U.S. Application Data

(60) Provisional application No. 60/552,229, filed on Mar. 11, 2004.

(51) Int. Cl.
*A61B 17/58* (2006.01)
(52) U.S. Cl. ............................... 606/67; 606/62
(58) Field of Classification Search ............ 606/62, 606/64, 65, 66, 67
See application file for complete search history.

(56) References Cited

U.S. PATENT DOCUMENTS

| | | | |
|---|---|---|---|
| 2,518,019 A | 8/1950 | Kane | |
| 3,433,220 A | 3/1969 | Zickel | |
| 4,622,959 A | 11/1986 | Marcus | |
| 4,776,330 A | 10/1988 | Chapman et al. | |
| 4,805,607 A | 2/1989 | Engelhardt et al. | |
| 4,827,917 A | 5/1989 | Brumfield | |
| 4,875,475 A | 10/1989 | Comte et al. | |
| 4,877,019 A | 10/1989 | Vives | |
| 4,946,459 A | 8/1990 | Bradshaw et al. | |
| 4,978,349 A | 12/1990 | Frigg | |
| 5,032,125 A | 7/1991 | Durham et al. | |
| 5,034,013 A | 7/1991 | Kyle et al. | |
| 5,074,882 A | 12/1991 | Grammont et al. | |
| 5,122,141 A | 6/1992 | Simpson et al. | |
| 5,127,913 A | 7/1992 | Thomas, Jr. | |
| 5,176,681 A | 1/1993 | Lawes et al. | |
| 5,201,735 A | 4/1993 | Chapman et al. | |
| 5,454,813 A | 10/1995 | Lawes | |
| 5,458,600 A | 10/1995 | Stapert et al. | |
| 5,489,284 A | 2/1996 | James et al. | |
| 5,505,733 A | 4/1996 | Justin et al. | |
| 5,505,734 A | 4/1996 | Caniggia et al. | |
| 5,549,610 A | 8/1996 | Russell et al. | |
| 5,569,249 A | 10/1996 | James et al. | |
| 5,620,445 A | 4/1997 | Brosnahan et al. | |
| 5,653,709 A | 8/1997 | Frigg | |
| 5,658,287 A | 8/1997 | Hofmann et al. | |
| 5,704,939 A | 1/1998 | Justin | |
| 5,766,174 A | 6/1998 | Perry | |
| 5,855,579 A | 1/1999 | James et al. | |
| 5,928,235 A | 7/1999 | Friedl | |
| 5,935,127 A | 8/1999 | Border | |
| 6,004,324 A | 12/1999 | Gahr et al. | |
| 6,106,528 A | 8/2000 | Durham et al. | |

(Continued)

FOREIGN PATENT DOCUMENTS

JP 9066061 3/1997

(Continued)

*Primary Examiner* — Nicholas Woodall
(74) *Attorney, Agent, or Firm* — Burgess Law Office, PLLC

(57) ABSTRACT

A fixation instrument for treating a bone fracture including a bone screw and a nail, wherein the bone screw extends through an opening in the head or proximal end of the nail. A movable insert is disposed within a chamber located at the proximal end of the nail. The insert engages the bone screw to prevent rotation thereof once the bone screw is placed in position.

20 Claims, 7 Drawing Sheets

U.S. PATENT DOCUMENTS

| | | |
|---|---|---|
| 6,228,086 B1 | 5/2001 | Wahl et al. |
| 6,235,031 B1 * | 5/2001 | Hodgeman et al. ............ 606/64 |
| 6,261,290 B1 | 7/2001 | Friedl |
| 6,406,477 B1 | 6/2002 | Fujiwara |
| 6,562,042 B2 * | 5/2003 | Nelson ............................ 606/62 |
| 6,648,889 B2 | 11/2003 | Bramlet et al. |
| 6,926,719 B2 * | 8/2005 | Sohngen et al. ................ 606/64 |
| 7,306,600 B2 * | 12/2007 | Roth et al. ...................... 606/53 |
| 2001/0012939 A1 * | 8/2001 | Wahl et al. ...................... 606/67 |
| 2001/0034523 A1 * | 10/2001 | Nelson ............................ 606/62 |
| 2002/0156473 A1 * | 10/2002 | Bramlet et al. ................. 606/62 |
| 2003/0074000 A1 * | 4/2003 | Roth et al. ...................... 606/62 |

FOREIGN PATENT DOCUMENTS

| | | |
|---|---|---|
| WO | WO 94/13219 | 6/1994 |
| WO | WO 96/35387 | 11/1996 |

\* cited by examiner

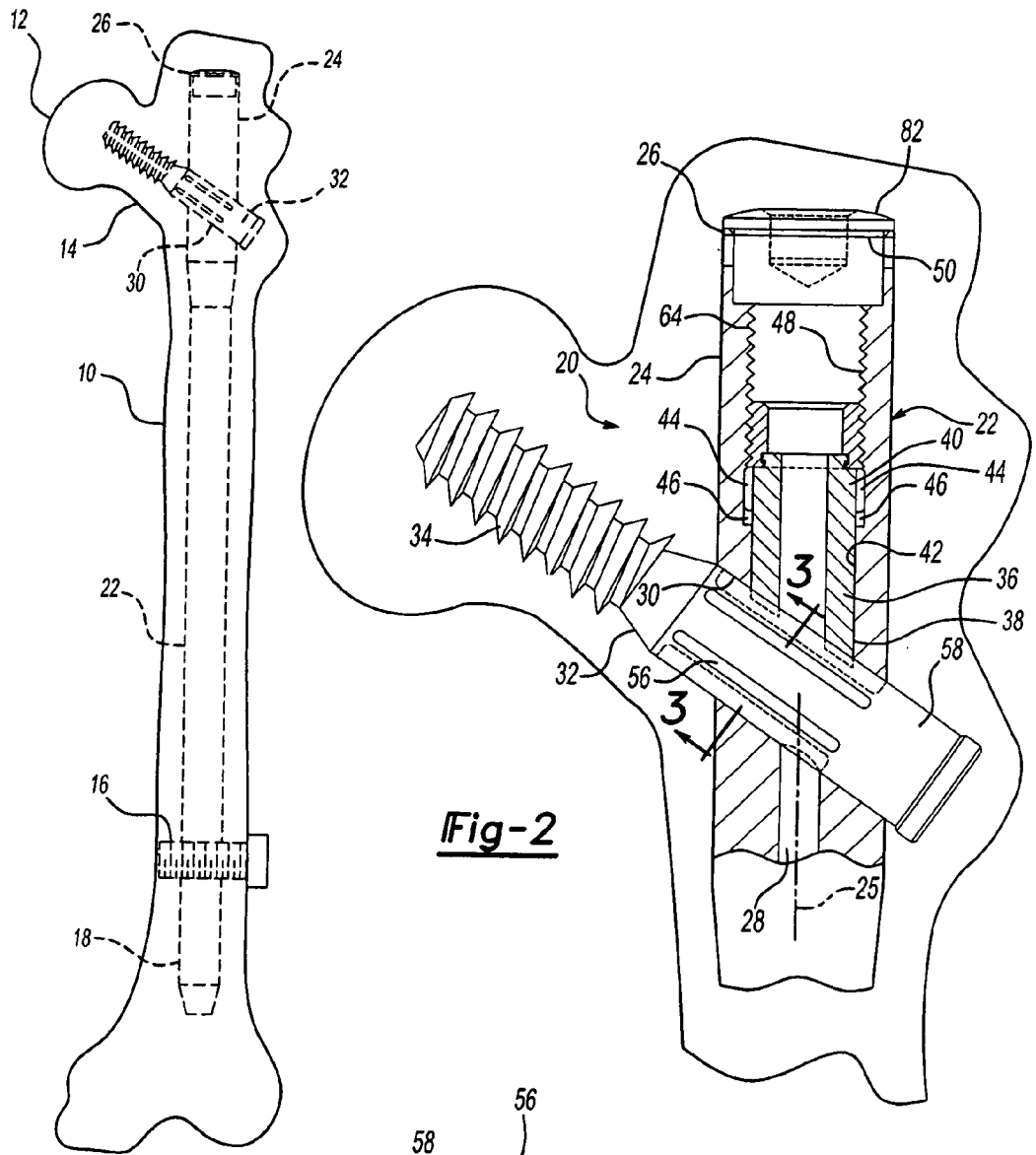
Fig-1
Fig-2
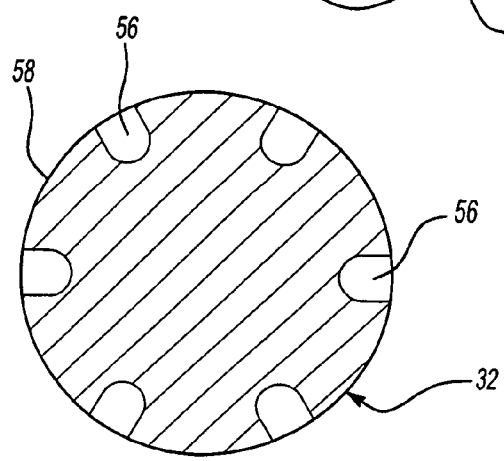
Fig-3

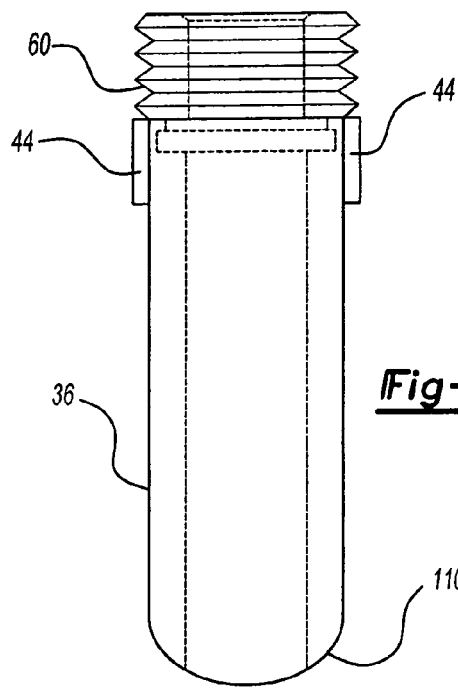
Fig-8B
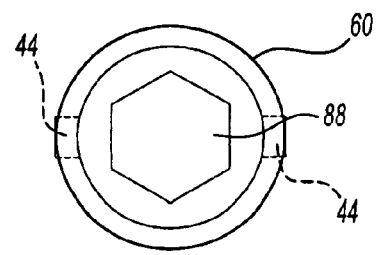
Fig-8C
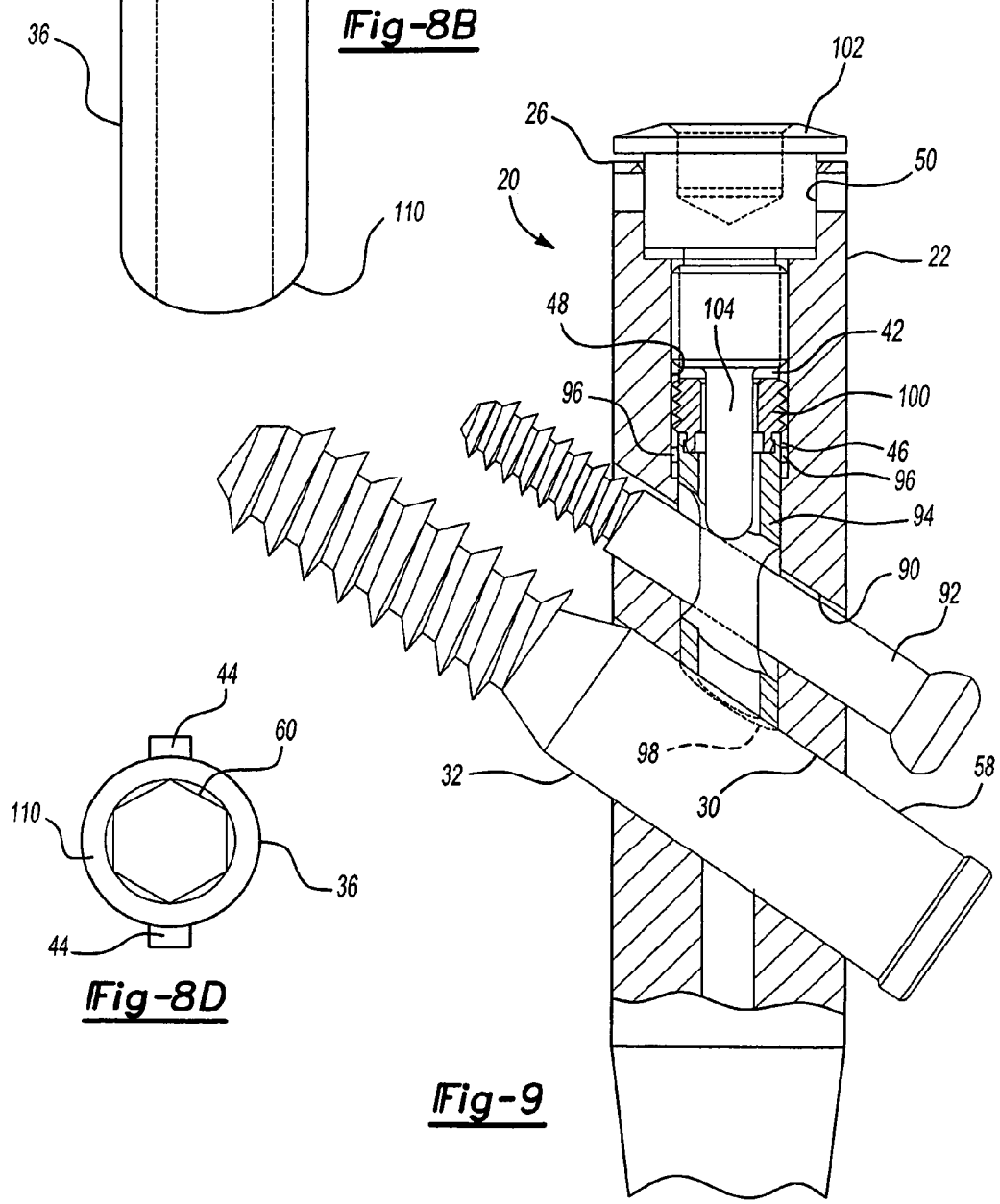
Fig-8D
Fig-9

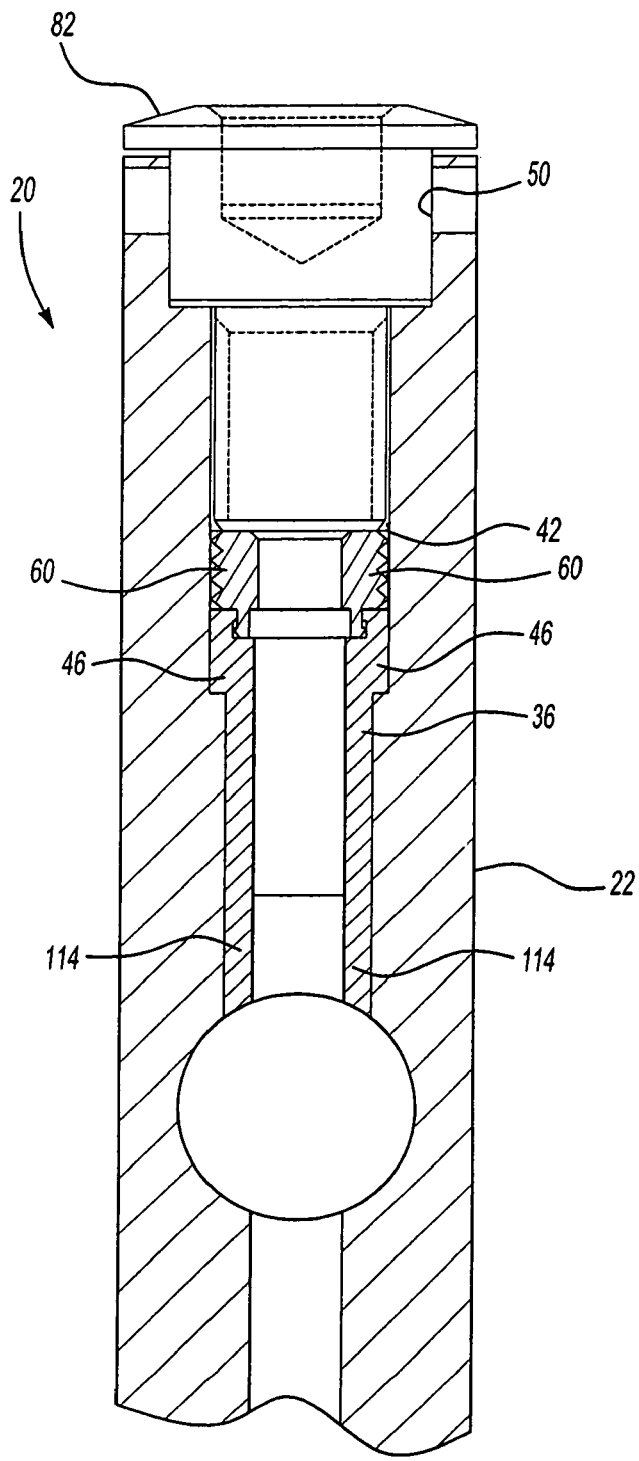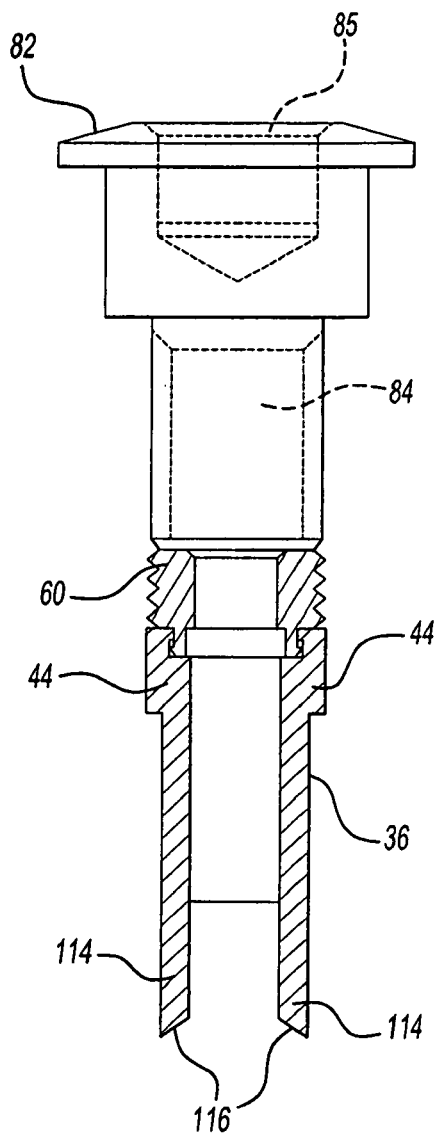
Fig-12
Fig-13

FIXATION INSTRUMENT FOR TREATING A BONE FRACTURE

CROSS-REFERENCE TO RELATED APPLICATIONS

This application claims the benefit of U.S. Provisional Application No. 60/552,229, filed Mar. 11, 2004.

BACKGROUND OF THE INVENTION

1. Field of the Invention

The present invention relates generally to a fixation instrument for treating bone fractures. More specifically, a nail and bone screw combination used to treat a fracture of the femur including trochanteric, intertrochanteric and femoral neck fractures.

2. Background of the Invention

Orthopedic fixation systems used for stabilizing a fracture often include an internal fixation device, typically an elongated implant such as a nail, screw or pin, inserted into the intramedullary canal of the bone to stabilize the fracture and promote healing. Such fixation systems are often used with a fracture of the femur. The femur generally includes an elongated shaft, a ball shaped head that fits into the hip socket and a neck connecting the ball to the shaft. The shaft also includes a greater trochanter and a lesser trochanter.

Typically, the nail is inserted in the marrow canal of the bone and is positioned to span the fracture. Nails are also used to treat fractures of the neck, head, intertrochanter, subtrochanteric, pathologic and certain ipsilateral shaft and neck fractures of the femur. For example, if the neck of the femur sustains a fracture a bone screw inserted through an aperture in the nail spans the fracture and threadably engages the femoral head.

Typically, the aperture in the end of the nail is a smooth bore in which the bone screw rotates as it threadably engages the femoral head. Once the bone screw is suitably tightened, it is left in place during the healing process. Bone screw migration is one problem that may occur during the healing process. Specifically, during loading or movement of the femur, the bone screw may migrate or loosen, thus creating a risk of failure at the fracture. Accordingly, there is in need for a fixation instrument that resists bone screw migration and rotation.

SUMMARY OF THE INVENTION

Accordingly, the present invention is a fixation instrument including a bone nail and bone screw combination for use in repairing a bone fracture. The bone nail extends within the shaft portion of a bone such as a femur. An opening in the head or proximal end of the nail receives a bone screw that, in the case of a femoral neck fracture, extends into the femoral head.

In accordance with an aspect of the present invention, a locking insert disposed within the nail engages the bone screw and prevents rotation thereof. Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 1 is a diagrammatic front view of a fixation instrument according to the present invention shown implanted within a femur.

FIG. 2 is an enlarged front view of the proximal end of the fixation instrument according to the present invention with portions removed for clarity and illustration.

FIG. 3 is a cross-sectional view of the bone screw shown in FIG. 2 taken along lines 3-3.

FIGS. 8A-8D are various views of an alternative embodiment of an insert for use with the fixation instrument according to the alternative embodiment of FIG. 7.

FIG. 9 is a front view of an additional alternative embodiment of a fixation instrument according to the present invention with portions removed for clarity and illustration.

FIG. 12 is a front view of a further alternative embodiment of a fixation instrument according to the present invention.

FIG. 13 is a front view, with portions removed for clarity, of the cap and insert assembly used in connection with the fixation instrument according to the embodiment of FIG. 12.

DETAILED DESCRIPTION OF THE INVENTION

Figure 4A:
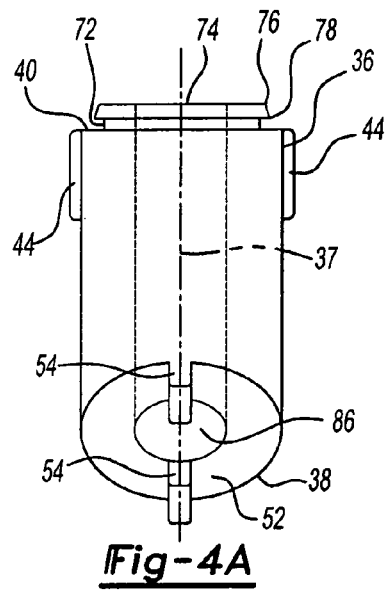
FIGS. 4A-4E are various views of an insert for use with the fixation instrument according to the present invention.
Figure 4B:
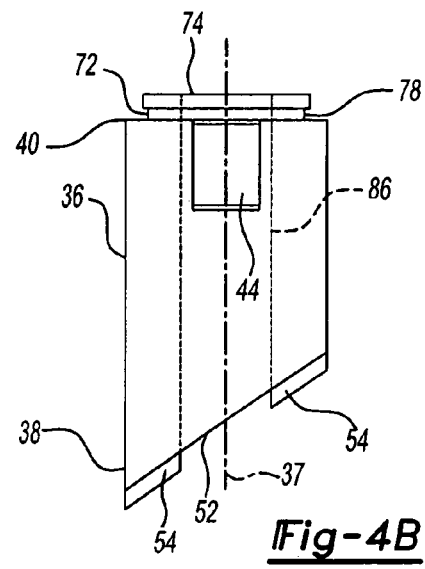
Figure 4C:
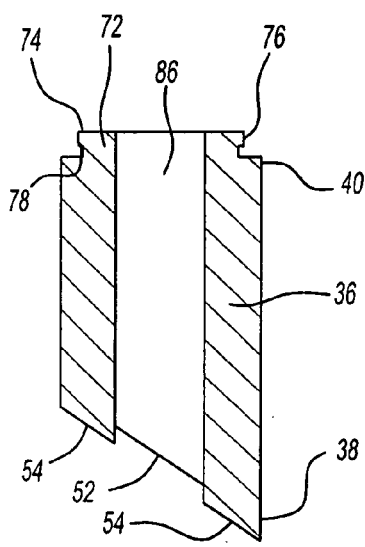
Figure 4D:
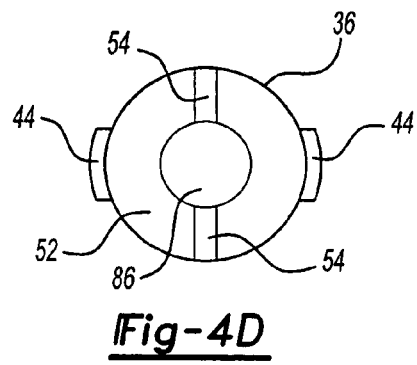
Figure 4E:
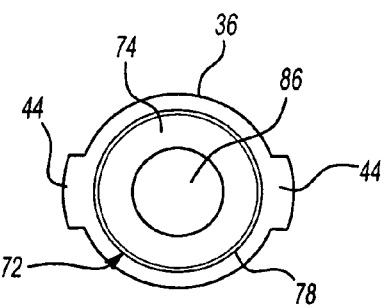

FIG. 1 shows a fixation instrument, seen generally at 20, according to one embodiment of the present invention placed in an assembled condition within a bone 10, illustrated here as a femur. The fixation instrument 20 includes a nail member 22 formed of a metallic alloy, such as a titanium alloy. The nail member 22 includes a distal end 18 and a proximal end 24. The distal end 18 typically includes at least one transverse aperture that receives a bone screw 16 used to fix the distal end 18 of the nail member 22 in place in the bone 10. The proximal end 24 includes a trailing or rear edge 26.

Turning now to FIGS. 2-6, a passageway 28 extends longitudinally through the nail member 22 between the proximal end 24 and the distal end 18. The passageway 28 receives insertion and extraction instrumentation, such as a guide wire (not shown), used to position the nail member 22 within the bone 10. Typically, the distal end 18 of the nail member 22 is inserted into the bone 10 first and follows the path of the guide wire.

The proximal end 24 includes an aperture 30 extending through the proximal end 24 in a direction that is typically angled with respect to the longitudinal axis 25 of the nail member 22. A bone screw 32 having a threaded portion 34 on one end thereof extends through the aperture 30 such that the threaded portion 34 engages the femoral head 12 for sliding compression of a femoral neck 14 or intratrochanteric fracture.

An insert 36 having a distal end 38 and a proximal end 40 is disposed within a chamber 42 located in the proximal end 24 of the nail member 22. The insert 36 further has a pair of tabs or guide/locating members 44 that extend radially outward from the body of the insert 36. The tabs or guide/locating members 44 cooperate with a pair of grooves or channels 46 that extend longitudinally along the sidewalls 48 of the chamber 42. The proximal end 24 of the nail member 22 includes an opening 50 at the trailing or rear edge 26 of the nail member 22. The opening 50 provides access to the chamber 42.

The insert 36 further includes a lower surface 52 having a pair of locking projections 54 extending longitudinally downward/outward from the lower surface 52. The insert 36 is placed in the chamber 42 through the opening 50, such that the tabs or guide/locating members 44 are received in the grooves or channels 46 located in the sidewalls 48 of the chamber 42. Accordingly, the insert 36 is slidably received and prevented from rotating in the chamber 42. The lower surface 52 of the insert 36 extends or is oriented at an angle that is substantially the same as the angle of the aperture 30 extending through the proximal end 24 of the nail member 22. As set forth below, the insert 36 engages the bone screw 32 disposed in the aperture 30 in the nail member 22.

The bone screw 32 further includes a plurality of longitudinally extending grooves 56 located on the outer surface 58 of the bone screw 32. The grooves 56 are of a size and shape that are complementary to the locking projections 54 located on the lower surface 52 of the insert 36. As seen in FIG. 2, when the insert 36 travels longitudinally in the chamber 42 it reaches a point wherein the lower surface 52 and locking projections 54 of the insert 36 are adjacent the bone screw 32. Since the purpose of the locking projections 54 is to engage the grooves 56 to secure and prevent rotation of the bone screw 32 it may be necessary to rotate the bone screw 32 slightly to align the grooves 56 of the bone screw 32 with the locking projections 54 of the insert 36. Once properly aligned, the insert 36 is driven further within or into the chamber 42 until the lower surface 52 of the insert 36 engages the outer surface 58 of the bone screw 32 and the locking projections 54 of the insert 36 extend into the grooves 56 of the bone screw 32.

Figure 5:
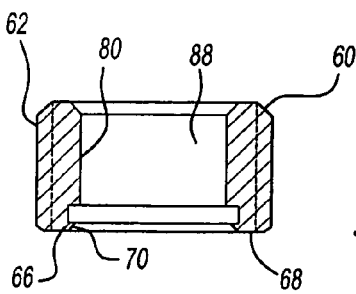
FIG. 5 is a side view of a locking ring for use with the fixation instrument according to the present invention.
Figure 6:
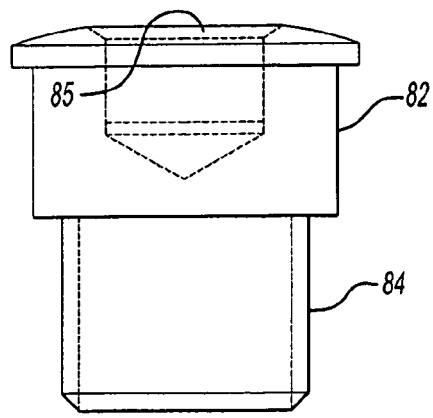
FIG. 6 is a side view of a cap for use with the fixation instrument according to the present invention.

A locking ring 60 controls the position of the insert 36 within the chamber 42. The locking ring 60 has a plurality of threads 62 disposed about the outer surface of the locking ring 60. The locking ring 60 threadably engages a plurality of threads 64 disposed on the sidewalls 48 of the chamber 42. As shown in FIG. 5, the locking ring 60 includes a post portion 66 located on or forming a portion of the lower surface 68 of the locking ring 60. The post portion 66 further includes an inwardly projecting finger 70. The post portion 66 may be formed as an annular member that extends all the way around the lower surface 68 or it may be formed as a plurality of individual post members spaced about the lower surface 68 of the locking ring 60.

The inwardly projecting finger 70 cooperates with a retaining member 72 formed on the upper surface 74 of the proximal end 40 of the insert 36. The retaining member 72 further includes an annular member 76 having an outwardly extending lip 78. Accordingly, the locking ring 60 is placed on or attached to the insert 36 using a snap or press fit arrangement. Specifically, the locking ring 60 is placed on the upper surface 74 of the insert 36 and a sufficient force is exerted on the locking ring 60 to deflect the inwardly projecting fingers 70 and correspondingly the post portion 66 outward over the annular member 76. Upon clearing the annular member 76, the fingers 70 snap back into place whereby they engage the underside of the lip 78 and rotatably secure the locking ring 60 to the insert 36. It should be understood that such an arrangement enables the locking ring 60 to rotate about the longitudinal axis 37 of the insert 36 while remaining attached to the insert 36.

The locking ring 60 has an aperture or opening 80 having a hexagonal shape that functions as a drive portion of the locking ring 60. Accordingly, a suitable tool, such as a T-handle hexagonal wrench, may be inserted into the opening 80 to rotate or turn the locking ring 60. This arrangement enables the insert 36 to be placed in the chamber 42 prior to the nail member 22 being inserted into the bone. Other configurations may function or comprise the drive portion, including putting a slot in the upper surface of the locking ring 60 that receives a driving tool such as a screwdriver.

The insert 36 is placed within the chamber 42 such that the tabs or guide/locating members 44 engage the grooves/channels 46 located in the sidewalls 48 of the chamber 42. Since the overall outer diameter of the insert 36 is less than the inner diameter of the threads 64 in the sidewalls 48 of the chamber 42, the insert 36 slides freely in the longitudinal direction and is constrained against rotation by the tabs or guide/locating members 44. As shown, the locking ring 60 is rotatably attached to the insert 36. Accordingly, when the threads 62 on the locking ring 60 engage the threads 64 in the sidewall 48 of the chamber 42 and when the locking ring 60 is rotated by a suitable tool, the locking ring 60 moves the insert 36 longitudinally within the chamber 42. As set forth above, the insert 36 and locking ring 60 combination is placed within the chamber 42 prior to inserting or installing the nail member 22 in the bone 10.

In use, once the nail member 22 is installed in the bone 10, the bone screw 32 is placed in and extends through the aperture 30 whereby it engages the femoral head 12. After tightening the bone screw 32 to compress the fracture, a suitable tool engages and rotates the locking ring 60 to move the insert 36 downwardly within the chamber 42 until the locking projections 54 engage the grooves 56 on the outer surface 58 of the bone screw 32. If necessary, it may be required to rotate the bone screw 32 slightly in order to have the locking projections 54 line up with the grooves 56. Once the insert 36 and bone screw 32 are properly aligned, tightening the locking ring 60 maintains engagement between the locking projections 54 and the grooves 56 and prevents rotation of the bone screw 32.

After tightening the locking ring 60, the opening 50 at the trailing or rear edge 26 of the nail member 22 is closed by a cap 82 threadably received in the chamber 42. The cap 82 includes a threaded post 84, the threads being of a suitable size and configuration to engage the threads 64 located in the sidewall 48 of the chamber 42. The cap 82 further includes a socket 85 suitable for receiving a driving tool to rotate and secure the cap 82 in the opening 50.

It should be understood that the insert 36 and locking ring 60 both have longitudinal passageways 86, 88 that allow the nail member 22 to be inserted within the bone 10 and follow a guide wire (not shown), with both the insert 36 and locking ring 60 installed or positioned within the chamber 42 of the nail member 22. Accordingly, the present invention enables the insert 36 to be pre-positioned or placed in the nail member 22 prior to installation, thus eliminating the need and difficulty of having to thread the insert 36 in place after the nail member 22 is placed within the bone 10.

Figure 7:
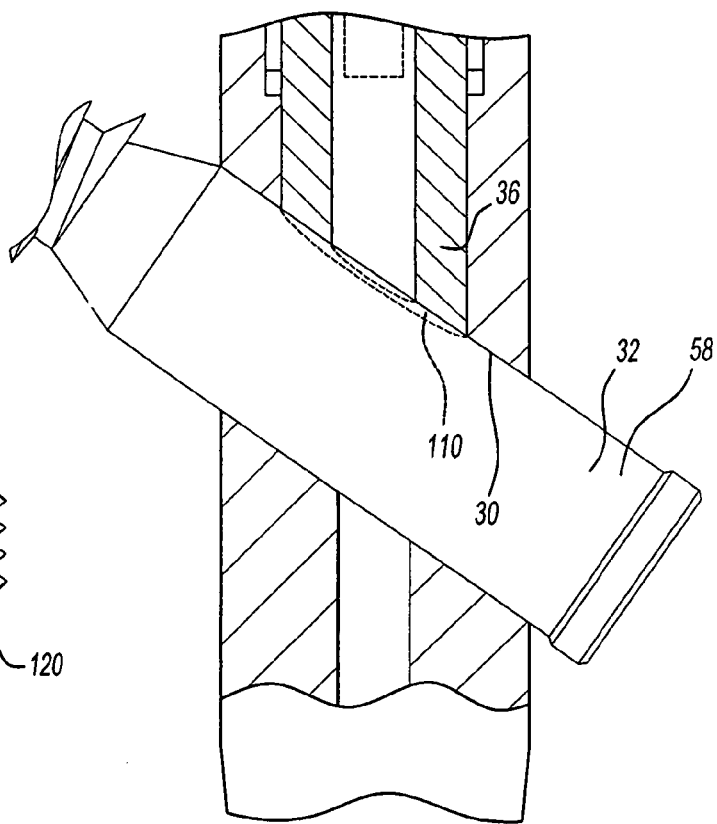
FIG. 7 is a front view of an alternative embodiment of a fixation instrument according to the present invention with portions removed for clarity and illustration.

FIGS. 7-8 disclose an additional embodiment of a fixation instrument 20, according to the present invention. Specifically, the lower surface 110 of the insert 36 has an arcuate surface having a shape complementary to the outer diameter of the bone screw 32. This embodiment does not use the locking projections of the previous embodiment, nor does the bone screw 32 have longitudinal grooves contained therein. The arcuate shape of the lower surface 110 creates a greater amount of surface area of the insert 36 that contacts the outer surface 58 of the bone screw 32. Thus, tightening the locking ring 60 provides a sufficient force to create friction fit between the insert 36 and the bone screw 32 that prevents rotation of the bone screw 32 within the aperture 30 of the nail member 22.

Figure 8A:
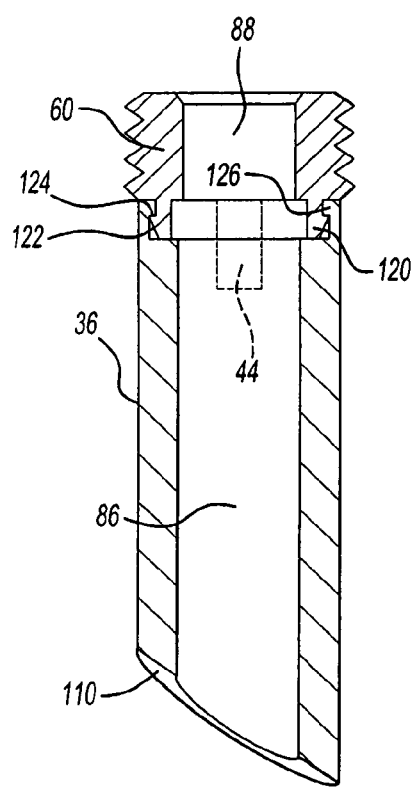
Figure 10A:
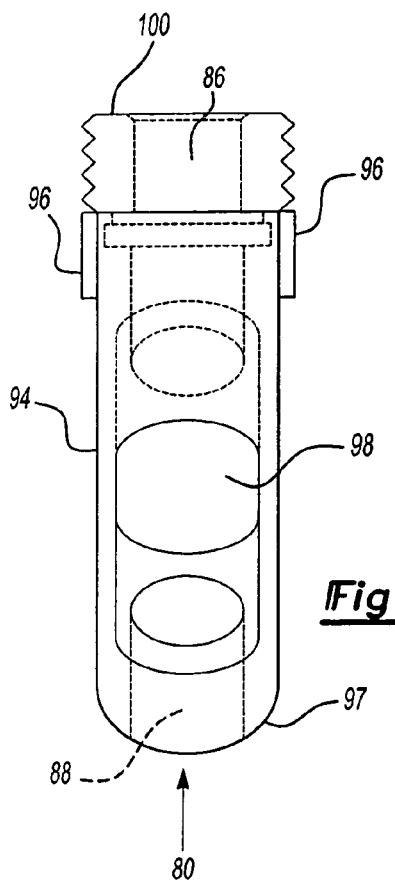
FIGS. 10A-10D are various views of the additional alternative embodiment of an insert for use with the fixation instrument according to the alternative embodiment of FIG. 9.
Figure 10B:
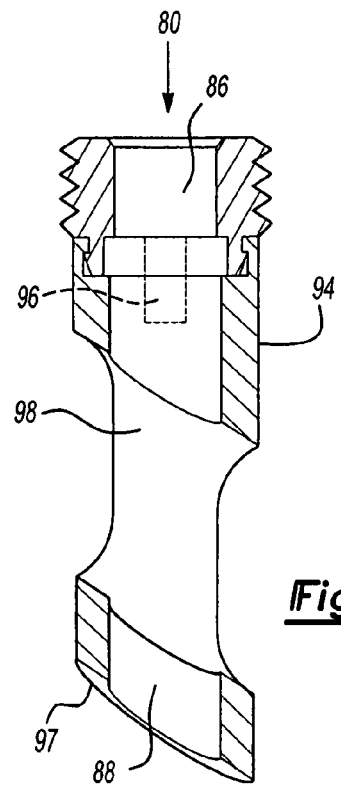
Figure 10C:
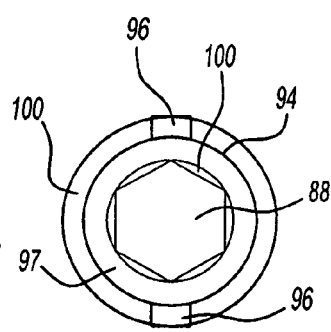
Figure 10D:
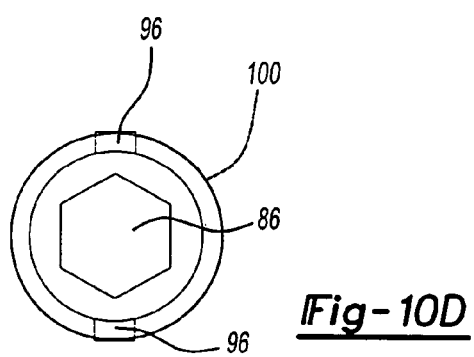

FIG. 8A further illustrates an alternative embodiment of a rotatable connection between the locking ring 60 and the insert 36. As shown therein, the locking ring 60 includes a downwardly projecting finger 120 having an inwardly beveled surface 122 and a lip 124. The insert 36 includes a inwardly extending flange 126. As with the previous embodiment, the locking ring 60 is rotatably attached to the insert 36 using a snap or press fit arrangement. Specifically, applying a force to the locking ring 60 causes the beveled surface 122 of the downwardly projecting finger 120 to engage the inwardly extending flange 126 and deflect the finger 120 radially inward until the lip 124 of the locking finger 120 clears the flange 126 and whereby the locking finger 120 snaps outwardly and the lip 124 engages the underside of the flange 126 to rotatably secure the locking ring 60 to the insert 36.

Figure 11:
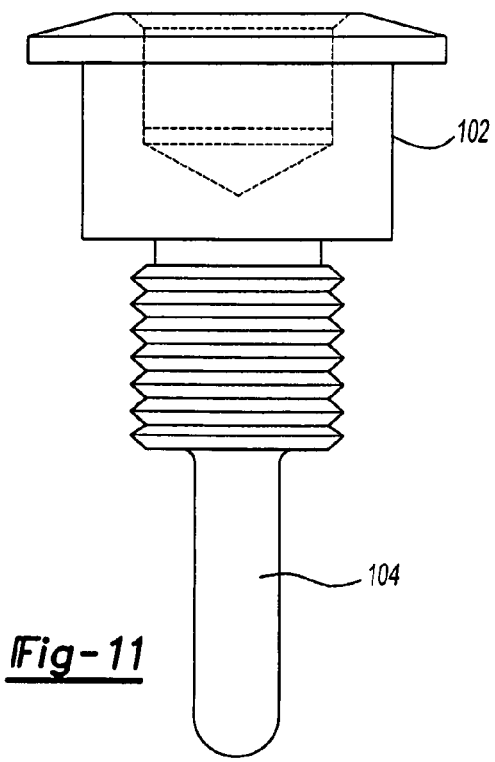
FIG. 11 is a side view of a cap for use with the fixation instrument according to the alternative embodiment of FIG. 9.
Figure 14:
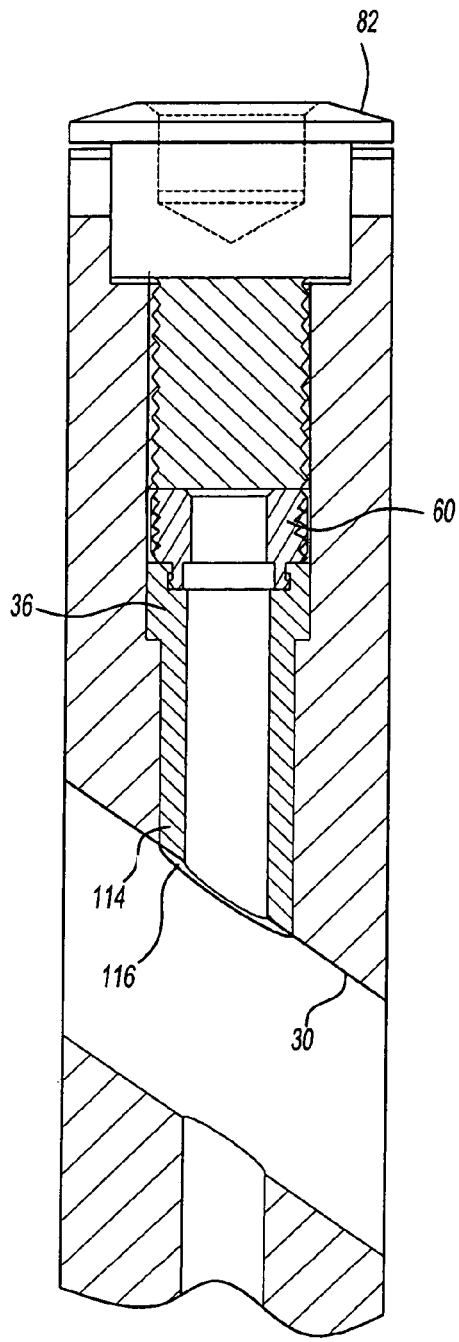
FIG. 14 is a side view of the further alternative embodiment of the fixation instrument shown in FIG. 12.
Figure 15:
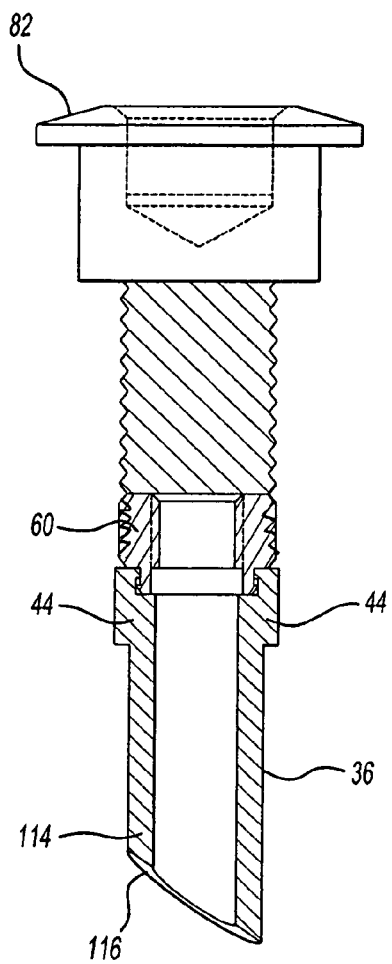
FIG. 15 is a side view of the cap and insert assembly shown in FIG. 12 used in connection with the fixation instrument according to the embodiment of FIG. 12, with FIG. 15A being a bottom view of the insert assembly of FIG. 15.
Figure 15A:
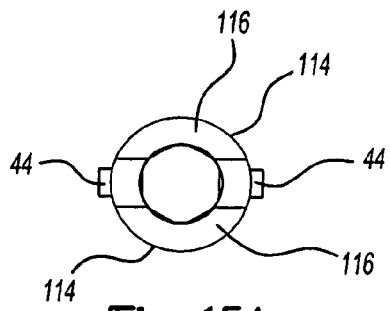

FIGS. 9-11 show an alternative embodiment of a fixation instrument 20 according to the present invention. As shown in FIG. 9, the proximal end 24 of the nail member 22 has an additional aperture 90 for receiving a second bone screw 92. As set forth in the previous embodiment, the insert 94 includes tabs or guide/locating members 96 that are received in the grooves/channels 46 located on the sidewalls 48 of the chamber 42 whereby the insert 94 is slidably fit within the chamber 42. The insert 94 has an arcuate lower surface 97 having a degree of curvature corresponding to the radius of the bone screw 32. Accordingly, as set forth above, rotating the locking ring 100 causes the arcuate lower surface 97 of the insert 36 to engage the outer surface 58 of the bone screw 32 to prevent rotation of the bone screw 32 within the aperture 30 of the nail member 22. The insert 94 also includes an aperture 98 extending at an angle with respect to the longitudinal axis of the insert 94 for receiving the second bone screw 92. The aperture 98 is elongated in the longitudinal direction to allow for travel of the insert 36 within the passageway 28 without engaging the second bone screw 92.

A cap 102 including an elongated tab or locking projection 104 is used to secure the second bone screw 92. When the cap 102 is inserted into the opening 50 on the trailing or rear edge 26 of the nail member 22, the elongated tab or locking projection 104 engages the second bone screw 92 to prevent rotation thereof via a frictional fit. In addition, the elongated tab or locking projection 104 may include and engagement portion which sits within a groove located on the second bone screw 92, as with the previous embodiments, to further prevent rotation of the second bone screw 92. This arrangement prevents rotation of both the first and second bone screws 32, 92 with respect to the nail member 22.

FIGS. 12-15 show a further alternative embodiment of a fixation instrument 20 according to the present invention, wherein the insert 36 has a lower surface formed of a pair of downwardly extending fingers 114. Each of the downwardly extending fingers 114 has an arcuate engagement surface 116 having a curvature or radius of curvature complementary to the diameter of the bone screw 32. The arcuate engagement surfaces 116 form the lower or contact surface of the insert 36. Accordingly, each of the fingers 114 engages the bone screw 32 to secure or prevent rotation of the bone screw 32 within the aperture 30. The insert 36 is positioned in and secured within the chamber 42 in a manner similar to the first embodiment. As with the previous embodiments, the locking ring 60 is used to position and secure the insert 36 whereby the arcuate engagement surfaces 116 of the fingers 114 engage the bone screw 32 and prevent rotation thereof.

It should be understood that the mounting relationship between the locking ring 60 and the insert 36 is one that enables the locking ring 60 to turn or rotate freely on the insert 36. In the case of the disclosed embodiments, the insert 36 travels longitudinally within the grooves or channels 46 located in the sidewalls 48 of the chamber 42. Thus, the apparatus and corresponding components forming the snap or press fit mounting relationship between the locking ring 60 and the insert 36, as shown in the disclosed embodiments, including the inwardly projecting finger and lip on the annular member, may be positioned on either the respective locking ring 60 or insert 36; i.e., the finger may be on the insert 36 or the locking ring 60 as long as the complementary component, the lip, is on the corresponding member.

Thus, it will be seen that the objects of the invention have been fully and effectively accomplished. It will be realized, however, that the foregoing specific embodiments have been shown and described for the purposes of illustrating the functional and structural principles of the invention and is subject to change without departure from such principles. Therefore, this invention includes all modifications encompassed within the scope of the following claims.

What is claimed is:

1. A fixation instrument for treating a bone fracture comprising:
    a nail member, said nail member having a longitudinal axis, a distal end and a proximal end, said proximal end having an aperture extending therethrough and said nail member having a chamber located in said proximal end;
    an insert having a longitudinal axis, said insert positioned and constrained against rotation about said longitudinal axis of said insert within said chamber;
    a bone screw, having a threaded portion, said bone screw extending through said aperture;
    a locking ring received in said chamber and engaging said insert, said locking ring operative to secure said insert within said chamber; and
    said insert having a distal end and a proximal end, a concave lower surface located at said distal end of said insert, said concave lower surface being that portion of the insert spaced farthest from the proximal end and engaging a convex surface of said bone screw, said convex surface complementary to said concave lower surface of said insert, when said bone screw extends through said aperture.

2. A fixation instrument for treating a bone fracture as set forth in claim 1 wherein said nail member has an opening adjacent a rear edge of said nail member to provide access to said chamber.

3. A fixation instrument for treating a bone fracture as set forth in claim 1 including said chamber having a plurality of threads located on an inner surface thereof;
    said locking ring having a plurality of threads located on an outer surface thereof, said threads on said locking ring complementary to said threads on said inner surface of said chamber; and
    said locking ring having a drive portion, whereby a suitable tool engages said drive portion and is used to move said locking ring.

4. A fixation instrument for treating a bone fracture as set forth in claim 1 including said concave lower surface having a shape complementary to an outer diameter of said bone screw.

5. A fixation instrument for treating a bone fracture as set forth in claim 4 including said aperture extending through said nail member at an angle with respect to the longitudinal axis of said nail member; and
said lower surface extending at an angle substantially the same as the angle of said aperture.

6. A fixation instrument for treating a bone fracture comprising:
a nail member, said nail member having a longitudinal axis, a distal end and a proximal end, said proximal end having an aperture extending therethrough and said nail member having a chamber located in said proximal end;
an insert adapted to be positioned within said chamber and having a lower surface, said lower surface operative to contact a bone screw extending through said aperture;
a locking ring received in said chamber and engaging said insert, said locking ring operative to secure said insert within said chamber;
a locking projection located on said lower surface of said insert; and
said bone screw having a longitudinally axis and having a plurality of longitudinal extending grooves, said grooves extending substantially parallel to said longitudinal axis of said bone screw on an outer surface of said bone screw wherein said locking projection is located in one of said grooves when said lower surface contacts said bone screw.

7. A fixation instrument for treating a bone fracture as set forth in claim 6 including said aperture extending through said nail member at an angle with respect to the longitudinal axis of said nail member; and
said lower surface extending at an angle substantially the same as the angle of said aperture.

8. A fixation instrument for treating a bone fracture as set forth in claim 6 wherein each of said insert and said locking ring have longitudinal passageways extending therethrough, wherein said longitudinal passageway extending through said insert terminates at said lower surface.

9. A fixation instrument for treating a bone fracture as set forth in claim 6 wherein said locking ring is rotatably connected to said insert.

10. A fixation instrument for treating a bone fracture as set forth in claim 9 wherein said locking ring includes a post portion having an inwardly projecting finger; and
said insert having a retaining member located on a distal end thereof, said retaining member including an outwardly extending lip wherein said locking finger engages said lip to rotatably secure said locking ring to said insert.

11. A fixation instrument for treating a bone fracture as set forth in claim 6 including a cap, said cap operative to close said opening located at said rear edge of said nail member.

12. A fixation instrument for treating a bone fracture as set forth in claim 6 wherein said lower surface is an arcuate surface.

13. A fixation instrument for treating a bone fracture comprising:
a nail member, said nail member having a longitudinal axis, a distal end and a proximal end, said proximal end having an aperture extending therethrough at an angle with respect to the longitudinal axis of said nail member and said nail member having a chamber located in said proximal end;
a bone screw;
an insert adapted to be positioned within said chamber, said insert having a proximal end and a distal end, said distal end terminating at said lower surface, said lower surface extending at an angle substantially the same as the angle of said aperture extending through said nail member and engaging said bone screw when said bone screw extends through said aperture;
a locking ring received in said chamber and engaging said insert, said locking ring operative to secure said insert within said chamber;
said nail member having a second aperture extending therethrough for receiving a bone screw; and
said insert having an aperture therein extending at an angle with respect to a longitudinal axis of said insert, said angle substantially the same as the angle of said second aperture extending through said nail member, said aperture for receiving a bone screw.

14. A fixation instrument for treating a bone fracture as set forth in claim 13 wherein said insert includes a longitudinal passageway extending through said insert;
said locking ring having a longitudinal passageway extending through said locking ring; and
a cap, said cap having an elongated locking projection, said elongated locking projection extending through said passageway in said locking ring and into said passageway in said insert, said elongated locking projection operative to engage a bone screw extending through said aperture in said insert.

15. A fixation instrument for treating a bone fracture as set forth in claim 14 wherein said locking ring is rotatably connected to said insert.

16. A fixation instrument for treating a bone fracture comprising:
a nail member, said nail member having a longitudinal axis, a distal end and a proximal end, said proximal end having an aperture extending therethrough at an angle with respect to said longitudinal axis, said nail member having a chamber located in said proximal end, said chamber having a plurality of threads located on an inner surface thereof and at least one groove located in said chamber;
an insert having a distal end and a proximal end adapted to be positioned within said chamber, said insert having at least one locating member, said locating member cooperating with said groove located in said chamber, said insert having a concave lower surface forming said distal end, said distal end and correspondingly said concave lower surface operative to engage a convex surface of said bone screw when said bone screw extends through said aperture; and
a locking ring received in said chamber and engaging said insert, said locking ring having a plurality of threads located on an outer surface thereof, said threads complementary to said threads on said inner surface of said chamber wherein said locking ring is threadably received in said chamber, said locking ring operative to secure said insert within said chamber.

17. A fixation instrument for treating a bone fracture as set forth in claim 16 wherein said locking ring is rotatably connected to said insert.

18. A fixation instrument for treating a bone fracture as set forth in claim 16 wherein said insert and said locking ring each have a longitudinal passageway extending therethrough.

19. A fixation instrument for treating a bone fracture comprising:

a nail member, said nail member having a longitudinal axis, a distal end and a proximal end, said proximal end having a plurality of apertures extending therethrough, each aperture extending at an angle with respect to said longitudinal axis and said nail member having a chamber located in said proximal end, said chamber having a plurality of threads located on an inner surface thereof and at least one groove located in said chamber;

an insert adapted to be positioned within said chamber, said insert having at least one locating member, said locating member cooperating with said groove located in said chamber, said insert including an aperture extending therethrough at an angle with respect to a longitudinal axis of said insert and including a longitudinal passageway extending therethrough, said insert having a lower surface, said longitudinal passageway extending to said lower surface, said lower surface operative to engage a bone screw extending through said aperture;

a locking ring received in said chamber and engaging said insert, said locking ring having a plurality of threads located on an outer surface thereof, said threads complementary to said threads on said inner surface of said chamber wherein said locking ring is threadably received in said chamber, said locking ring having a longitudinal passageway therethrough and a drive portion suitable to receive a tool used to rotate said locking ring in said chamber, said locking ring operative to secure said insert within said chamber; and a cap, said cap threadably received in said chamber and having an elongated locking projection, said elongated locking projection extending into said passageway and said locking ring and said insert and operative to engage a bone screw extending through said aperture in said insert.

20. A fixation instrument for treating a bone fracture as set forth in claim 19 including said aperture extending through said nail member at an angle with respect to the longitudinal axis of said nail member; and said lower surface extending at an angle substantially the same as the angle of said aperture.

\* \* \* \* \*